United States Patent [19]

Hanifl et al.

[11] Patent Number: 5,085,633
[45] Date of Patent: Feb. 4, 1992

[54] METHOD OF FORMING SUCTION SWAB

[75] Inventors: Paul H. Hanifl, Barrington; Donald R. Harreld, Woodstock, both of Ill.

[73] Assignee: Sage Products, Inc., Crystal Lake, Ill.

[21] Appl. No.: 717,858

[22] Filed: Jun. 19, 1991

Related U.S. Application Data

[63] Continuation of Ser. No. 570,886, Aug. 22, 1990, abandoned.

[51] Int. Cl.$^5$ ............................................. A61M 1/00
[52] U.S. Cl. ................................. 604/35; 29/450; 29/451; 604/73; 604/264; 604/268; 604/313; 408/19; 408/1 R
[58] Field of Search ............... 604/35, 73, 264, 268, 604/313; 408/19, 1 R; 29/450, 451, 33 K; 15/393, 415.1; 433/91, 93, 96

[56] References Cited

U.S. PATENT DOCUMENTS

| | | | |
|---|---|---|---|
| 2,595,666 | 5/1952 | Hutson | 433/96 |
| 3,758,950 | 9/1973 | Krouzian | 433/91 |
| 3,864,831 | 2/1975 | Drake | 433/91 |
| 4,605,344 | 8/1986 | Hartmann | 408/1 R |
| 4,704,435 | 2/1978 | Orsing | 433/96 |
| 4,864,713 | 9/1989 | Roberts et al. | 29/33 K |

Primary Examiner—P. W. Echols
Assistant Examiner—David P. Bryant
Attorney, Agent, or Firm—Lee, Mann, Smith, McWilliams & Sweeney

[57] ABSTRACT

A method of forming a disposable suction swab from an elongated stem having an enlarged, resilient tip at one end. The stem is installed in a longitudinal central channel in the tip, and the assembly is then compressed between a pair of displaceable clamp plates, the plates having drill apertures in registration with one another and with the tip being in alignment with the apertures. A hole is then bored through the compressed tip and stem by drilling through the apertures in the clamp plates. The plates are released to eject the formed swab.

9 Claims, 1 Drawing Sheet

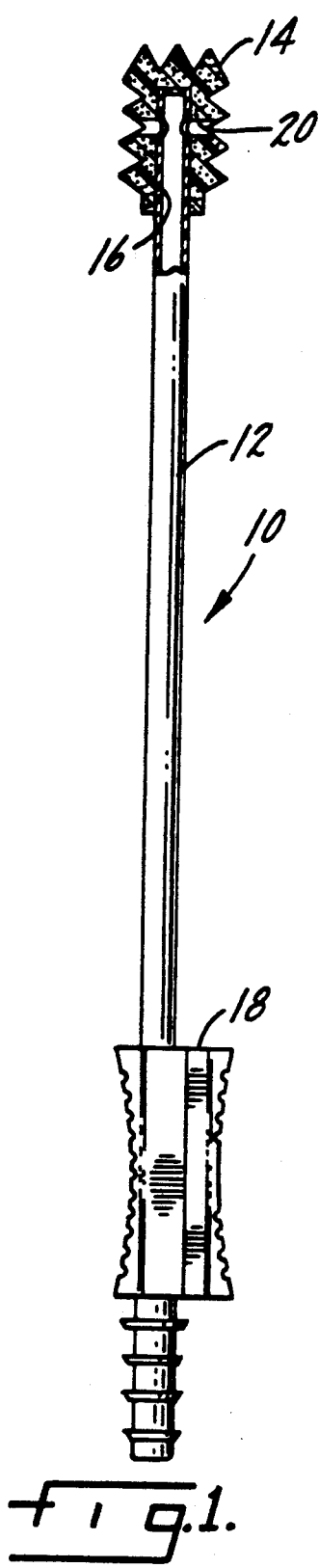
Fig. 1.
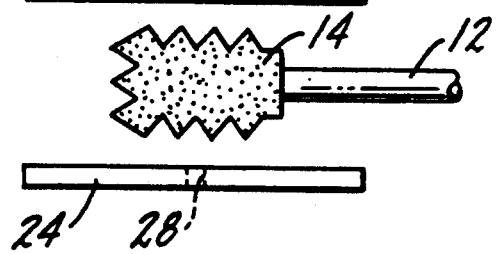
Fig. 2.
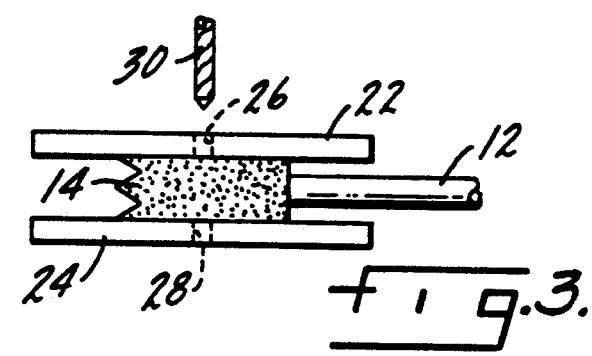
Fig. 3.
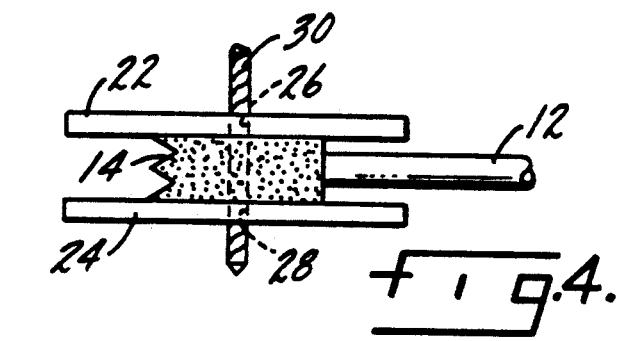
Fig. 4.
Fig. 5.

METHOD OF FORMING SUCTION SWAB

This application is a continuation of application Ser. No. 570,886, filed Aug. 22, 1990, now abandoned.

BACKGROUND OF THE INVENTION

This invention relates to oral swabs, and in particular to a method of forming an oral swab so that the swab can be used in connection with a source of suction to eliminate body fluids of a patient.

As explained in detail in co-pending application Ser. No. 496,423, filed Mar. 20, 1990, the disclosure of which is incorporated herein by reference, oral swabs are used for mouth care. Typically, the swabs are discarded after having been used. The referenced application describes a suction swab which can be connected to a source of suction for removing liquids and small solids.

The swab of the referenced application is formed by a multi-step process. While the resulting swab has great utility, the process is a bit complicated, and therefore expensive. Furthermore, the process involved leads, at times, to unsatisfactory accumulations of adhesive in the suction apertures in the tip of the swab, resulting in a defective product.

SUMMARY OF THE INVENTION

The present invention is directed to a method of forming a disposable suction swab. First, a resilient, compressible tip is installed on an end of an elongated, hollow stem, with the tip enveloping the end of the stem. The thus-installed tip is then located between a pair of displaceable clamp plates, each of the plates having a drill aperture, with the apertures being in registration and with the tip being in alignment with the apertures. The tip is then compressed between the plates with the stem being located between the apertures. Thereafter, a hole is bored through the compressed tip and the hollow stem by drilling through the apertures in the plates. Finally, the then-completed swab is released from the plates.

In accordance with the preferred form of the invention, the step of boring the hole comprises drilling completely through the apertures of the compressed plates. Preferably, compression of the tip of the swab occurs without distortion of the shape of the stem.

In accordance with the disclosed and preferred from of the invention, the tip of the swab is made of foam having an open cell structure. The step of compressing the tip between the plates comprises compressing the tips sufficiently to collapse the cell structure of the foam.

BRIEF DESCRIPTION OF THE DRAWING FIGURES

The invention is described in greater detail in the following description of an example embodying the best mode of the invention, taken in conjunction with the drawing figures, in which:

FIG. 1 is a side-elevational illustration of a suction swab according to the invention, partly in cross section to illustrate detail;

FIG. 2 is a side-elevational illustration of the first step of the boring process according to the invention, where the stem and tip are located between a pair of displaceable clamp plates;

FIG. 3 is a side-elevational illustration similar to FIG. 2, but with the clamp plates closed to compress the tip between the plates;

FIG. 4 is a side-elevational illustration similar to FIG. 3, but with the drill bit having passed through the apertures in the plates and the swab which is sandwiched therebetween; and FIG. 5 is a side-elevational illustration similar to FIG. 2, subsequent to the boring operation and release of the swab from between the plates.

DESCRIPTION OF AN EXAMPLE

Embodying the Best Mode of the Invention

A disposable suction swab resulting from and according to the invention is shown generally at 10 in the drawing figures. The swab 10 is composed of an elongated, hollow stem 12 on which an enlarged, resilient and compressible tip 14 is mounted. The stem 12 may be of plastic, and the tip 14 is preferably made of a pliant cellular foam, or other similar, soft structure which is liquid absorbent. The tip 14 is preferably ribbed as shown or formed otherwise to promote scrubbing when the swab 10 is used.

The tip 14 has a longitudinal central channel 16 which accommodates the stem 12, the stem being suitably affixed to the tip 14 by means of an adhesive or other appropriate material. The end of the swab 10 opposite to the tip 14 is installed within a suction port 18. The suction port 18 does not form any part of the present invention, and is described in detail in referenced U.S. patent application Ser. No. 496,423.

The swab 10 includes a transverse hole 20 extending therethrough. The hole 20 is formed in accordance with the process illustrated in FIGS. 2 through 5, that process being described immediately below.

After the tip 14 has been installed on the stem 12, the tip 14 and stem 12 are located between a pair of displaceable clamp plates 22 and 24. The plate 22 includes a drill aperture 26, and the plate 24 includes a drill aperture 28. As can be seen, the drill apertures 26 and 28 are in registration with one another.

After the swab has been appropriately oriented between the plates 22 and 24, the plates are clamped against the swab, compressing the tip 14 as illustrated in FIG. 3. With the tip 14 thus compressed, and protected between the plates 22 and 24, the tip 14 can be drilled without tearing of the foam structure of the tip 14 that would occur if the tip 14 were not held tightly between the plates 22 and 24. The means of operation of the plates 22 and 24 to clamp the plates as illustrated is not shown in the drawing figures, and may be any conventional, well-known apparatus.

After the plates 22 and 24 have been closed as illustrated in FIG. 3, a drill 30 is used to bore the hole 20 through the tip 14, through the stem 12 and entirely through the sandwiched assembly of the plates 22 and encapsulated swab 10 therebetween. Thereafter, the drill 30 is withdrawn, and the plates 22 and 24 are opened to release the tip 14 from between the plates.

The plates 22 and 24 exert sufficient pressure when brought to bear upon the tip 14 so that the tip 14 can be drilled by the drill 30 without tearing of the cellular foam material or other material of the tip 14. If formed of a cellular foam, the tip 14 is crushed sufficiently to collapse the cell structure of the foam for the drilling operation. However, the plates 22 and 24 do not exert undue pressure sufficient to distort the shape of the stem 12. The amount of force exerted by the plates 22 and 24 will depend on the wall strength of the stem 12, the type of foam or other material forming the tip 14, and the type of drill bit 30 employed.

Various changes can be made to the invention without departing from the spirit thereof or scope of the following claims.

What is claimed is:

1. A method of forming a suction swab, comprising the steps of
   a. installing a resilient compressible tip on an end of an elongated, hollow stem, with the tip enveloping the end of the stem,
   b. locating the tip between a pair of displaceable clamp plates, the plates each having a drill aperture, with the apertures being in registration with each other and with the tip being in alignment with the apertures,
   c. compressing the tip between the plates with the stem being located between the apertures,
   d. boring a hole through the compressed tip and the hollow stem by drilling through said apertures, and
   e. releasing the tip from the plates.

2. The method according to claim 1 in which method step "d" comprises drilling completely through the apertures of the compressed plates.

3. The method according to claim 1 in which method step "c" comprises compressing the tip without distorting the shape of the stem.

4. The method according to claim 1 in which the tip is made of foam having a cell structure, and method step "c" comprises compressing the tip, thereby collapsing the cell structure of the foam.

5. A suction swab formed in accordance with the method of claim 1, wherein said end of the hollow stem is sealed by said compressible tip and said hole extends laterally through said tip with respect to said hollow stem, is generally round in cross section with a generally constant diameter, and is the only hole in said swab for application of suction to the tip.

6. A method of forming a suction swab, comprising the steps of
   a. forming a resilient, compressible foam tip for the swab, with the tip having a longitudinal central channel,
   b. installing the tip on an end of an elongated, hollow stem, with the end of the stem being located in the channel,
   c. locating the tip between a pair of displaceable clamp plates, the plates each having a drill aperture, with the apertures being in registration with each other and with the tip being in alignment with the apertures,
   d. compressing the tip between the plates, thereby compressing the foam, with the stem being located between the apertures,
   e. boring a hole through the compressed tip and the hollow stem by drilling through said apertures, and
   f. releasing the tip from the plates.

7. The method according to claim 6 in which method step "e" comprises drilling completely through the apertures of the clamp plates.

8. The method according to claim 6 in which method step "d" comprises compressing the tip without distorting the shape of the stem.

9. A suction swab formed in accordance with the method of claim 6, wherein said end of the hollow stem is sealed by said compressible tip and said hole extends laterally through said tip with respect to said central channel, is generally round in cross section with a generally constant diameter, and is the only hole in said swab for application of suction to the tip.

* * * * *